(12) United States Patent
Taya et al.

(10) Patent No.: US 7,297,517 B2
(45) Date of Patent: Nov. 20, 2007

(54) **OLIGONUCLEOTIDES AND METHOD FOR DETECTION OF MECA GENE OF METHICILLIN-RESISTANT *STAPHYLOCOCCUS AUREUS***

(75) Inventors: Toshiki Taya, Sagamihara (JP); Takahiko Ishiguro, Yokohama (JP); Juichi Saito, Yamato (JP)

(73) Assignee: Tosoh Corporation, Yamaguchi-ken (JP)

( * ) Notice: Subject to any disclaimer, the term of this patent is extended or adjusted under 35 U.S.C. 154(b) by 18 days.

(21) Appl. No.: 09/865,579

(22) Filed: May 29, 2001

(65) Prior Publication Data

US 2002/0098492 A1 Jul. 25, 2002

(30) Foreign Application Priority Data

May 29, 2000 (JP) ........................................ 2000-163149
Jun. 9, 2000 (JP) ........................................ 2000-179394

(51) Int. Cl.
    *C12P 19/34* (2006.01)

(52) U.S. Cl. ..................................... 435/91.2; 435/91.1
(58) Field of Classification Search ................ 435/91.1, 435/91.2, 6; 536/23.1, 24.3
    See application file for complete search history.

(56) References Cited

U.S. PATENT DOCUMENTS 5,994,066 A 11/1999 Bergeron et al. .............. 435/6
6,136,533 A * 10/2000 Bekkaoui et al.

FOREIGN PATENT DOCUMENTS

| EP | 0 639 647 | 2/1995 |
| EP | 0855447 | 7/1998 |
| EP | 1 035 214 | 9/2000 |
| WO | WO 95/13395 | 5/1995 |
| WO | WO 99/01572 | 1/1999 |

OTHER PUBLICATIONS

Ryffel et al. (Gene, 94 (1999) 137–138).*
Ishiguro et al. (Nucleic Acids Research, 1996, vol. 24, No. 24, pp. 4992–4997).*
M.D. Song et al., FEBS Lett., vol. 221, No. 1, pp. 167–171 (1987) "*Evolution of an inducible penicillin–target protein in methicillin–resistant Staphylococcus aureus by gene fusion.*", Elsevier Science Publishers B. V.
Steven M. Salisbury et al., "Identification of methicilli–resistant staphylococci by multiplex polymerase chain reaction assay", American Journal of Clinical Pathology, vol. 107, No. 3, 1997, pp. 368–373.
Shohei Kagawa et al., "MRSA—detection of mecA and its regulatory genes", Rinsho Byori, The Japanese Journal of Clinical Pathology, Nov., 1993, vol. 41, No. 11, pp. 1223–1231.
T. Ito, et al., "Cloning and nucleotide sequence determination of the entire mec DNA of pre–methicillin–resistant *Staphylococcus aureus* N315", Antimicrobial Agents and Chemotheraphy, vol. 43, No. 6, Jun., 1999, pp. 1449–1458.
Chin, "On the Preparation and Utilization Isolated and Purified Oligonucleotides", University of North Carolina School of Law, first 3 pages, 2002.
Chin, The unabridged electronic version of the article "On the Preparation and Utilization of Isolated and Purified Oligonucleotides", "README", 2002.
European Search Report relating to EP Patent application (EPA 04 026 759.3).
Chan, Alan B., et al., "NASBA and other transcription–based amplification methods for research and diagnostic microbiology," Reviews in Medical Microbiology (1999), vol. 10(4), pp. 185–196.

* cited by examiner

*Primary Examiner*—Juliet C. Switzer
(74) *Attorney, Agent, or Firm*—DLA Piper US LLP

(57) ABSTRACT

An oligonucleotide for cleavage, detection or amplification of the mecA gene, a gene element of methicillin-resistant *Staphylococcus aureus* (MRSA), or RNA derived from said gene is provided. Further, a method for detecting the mecA gene is provided.

4 Claims, 5 Drawing Sheets

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 1 tttttttattt tacgatcctg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 2
ctcgtttttt atttttagat                                               20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 3
gtagtttgtt ttaatttat                                                20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 4
cacataccat cttctttaac                                               20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene
```

-continued

```
<400> SEQUENCE: 5
tgtttcggtc taaaatttta                                              20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 6
ttataatctt ttttagatac                                              20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 7
atacttagtt ctttagcgat                                              20

<210> SEQ ID NO 8
<211> LENGTH: 39
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 8
cccaattttg atccatttgt tgttgatata gtcttcaga                         39

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 9 attttttgc gaaatcactt                                               20

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 10 ttttctttt ctctattaat g                                             21

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 11
```
gttagttgaa tatctttgcc                                                  20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 12
atttattata ttcttcgtta                                                  20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 13 ttcttttta tcttcggtta                                                   20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 14
tcattgctgt taatatttt                                                   20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 15
ctttgttttt cgtgtctttt                                                  20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 16
ttaatagatt gatattttct                                                  20

<210> SEQ ID NO 17
<211> LENGTH: 14
<212> TYPE: DNA
<213> ORGANISM: Artificial Sequence
<220> FEATURE:
<223> OTHER INFORMATION: Oligonucleotide capable of binding specifically
      to mecA gene or RNA derived from said gene

<400> SEQUENCE: 17
gaaggtgtgc ttac                                                        14

```
<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
aaattgggta caagatgata ccttcgtt                                          28

<210> SEQ ID NO 19
<211> LENGTH: 14
<212> TYPE: DNA
<213> ORGANISM: Artificial Sequence
<220> FEATURE:
<223> OTHER INFORMATION: Primer

<400> SEQUENCE: 19
gaaggtgtgc ttac                                                         14

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ttttcttttt ctctattaat g                                                 21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gttagttgaa tatctttgcc                                                   20

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
aaagaaaaaa gatggcaaag atattcaa                                          28

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ttctttttta tcttcggtta                                                   20

<210> SEQ ID NO 24
<211> LENGTH: 20
<212> TYPE: DNA
<213> ORGANISM: Artificial Sequence
<220> FEATURE:
<223> OTHER INFORMATION: Primer
```

```
<400> SEQUENCE: 24
tcattgctgt taatattttt                                              20

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
caactaacta ttgatgctaa agttcaaa                                     28

<210> SEQ ID NO 26
<211> LENGTH: 39
<212> TYPE: DNA
<213> ORGANISM: Artificial Sequence
<220> FEATURE:
<223> OTHER INFORMATION: Probe

<400> SEQUENCE: 26
cccaattttg atccatttgt tgttgatata gtcttcaga                         39

<210> SEQ ID NO 27
<211> LENGTH: 39
<212> TYPE: DNA
<213> ORGANISM: Artificial Sequence
<220> FEATURE:
<223> OTHER INFORMATION: Probe

<400> SEQUENCE: 27 ttttctttt ctctattaat gtatgtgcga ttgtattgc                          39

<210> SEQ ID NO 28
<211> LENGTH: 39
<212> TYPE: DNA
<213> ORGANISM: Artificial Sequence
<220> FEATURE:
<223> OTHER INFORMATION: Probe

<400> SEQUENCE: 28
gttagttgaa tatctttgcc atctttttc tttttctct                          39

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tgtttgaggg tggatagcag                                              20

<210> SEQ ID NO 30
<211> LENGTH: 28
<212> TYPE: DNA
<213> ORGANISM: T7 phage
<220> FEATURE:
<221> NAME/KEY: promoter
<223> OTHER INFORMATION: Promoter sequence of T7 polymerase

<400> SEQUENCE: 30
aattctaata cgactcacta tagggaga                                     28
```

OLIGONUCLEOTIDES AND METHOD FOR DETECTION OF MECA GENE OF METHICILLIN-RESISTANT *STAPHYLOCOCCUS AUREUS*

FIELD OF THE INVENTION

The present invention relates to oligonucleotides and method for detecting methicillin-resistant *Staphylococcus aureus* (MRSA) in clinical examination. The oligonucleotides provided in the present invention are useful as reagents for genetic diagnosis which involves procedures such as cleavage, amplification and detection of RNA or DNA, and as reagents for inhibiting reverse transcription or translation of RNA. In particular, the sequences of the oligonucleotides provided in the present invention are useful for reagents or the like for quantitative determination and diagnosis of MRSA.

PRIOR ART

MRSA is a resistant strain of *Staphylococcus aureus* exhibiting resistance against β-lactamase-resistant penicillins, including methicillin, which are stable against β-lactamase produced by *Staphylococcus aureus*. MRSA is a major pathogen in the nosocomial infections, and strains thereof which exhibit a slight resistance even to vancomycin, an effective therapeutic drug against the resistant strain, have also been detected. MRSA is causing significant problems in medical care due to the lack of an effective antimicrobial drug thereto. Thus, its accurate and rapid detection in clinical examination is an important subject in diagnosis and treatment.

*Staphylococcus aureus* generally produces four types of cell wall composing-proteins PBPS(penicillin-binding proteins), i.e., PBP-1 through PBP-4, however, it had been found that MRSA also produces a new type of PBP termed PBP-2'. This type of PBP is a specific protein having poor affinity against β-lactam antibiotics, and is known to play a central role in the tolerance of this organism. The sequence of the mecA gene that codes for PBP-2' is known (FEBS Lett., 221, 167–171, 1987, etc.). Therefore, hybridization methods employing a gene probe specific to mecA gene have been sought to detect and identify MRSA.

As mentioned above, although attempts have been made to detect MRSA at the gene level, since preparation of a sample requires culturing the bacteria obtained from a patient specimen, these methods have problems in terms of their speed. Since detection and identification of MRSA requires long culturing period, and it is difficult to rapidly detect a trace amount of mecA gene in a sample, there is a need for the development of a rapidly and highly sensitive detection method in the field of clinical diagnosis. Moreover, there is also a need to develop an automated examination apparatus to simplify examinations.

In order to carry out highly sensitive detection, it is preferable to perform said detection after amplifying a specific sequence in the gene to be detected and identified, or in RNA derived from said gene (hereafter, referred to as the "target nucleic acid").

When the target nucleic acid is DNA, the Polymerase chain reaction (PCR) method is known as an amplification method. This method amplifies a specific sequence by repetition of a cycle comprising heat denaturation, primer annealing and extension reactions, in the presence of a pair of primers complementary and homologous to both ends of said specific sequence in the target DNA as well as a thermostable DNA polymerase. At this time, in order to amplify said specific sequence by PCR, oligonucleotides that are highly specific to said specific sequence are required. Moreover, in order to carry out this detection and identification with high sensitivity, oligonucleotides that are highly specific to the target DNA are required. Further, it is also necessary to determine the optimum combination of those oligonucleotides. Therefore, attempts have been made to detect the mecA gene located on the chromosomal DNA of *Staphylococcus aureus* by PCR using specific oligonucleotides sequences. However, in order to prepare a sample, it is necessary to culture the bacteria obtained from a patient specimen. Therefore, as in the hybridization method mentioned above, there is a problem in terms of their speed. In addition, since the detection of the mecA gene located on the chromosomal DNA does not actually lead to an identification of the expression of PBP-2', there are also problems in terms of clinical significance. Further, the PCR method requires a complicated procedure involving repetition of rapidly increasing and decreasing the temperature, which prevents its automation.

On the other hand, as amplification methods in cases where the target nucleic acid is RNA, in addition to the RT-PCR method, there are known the NASBA method and 3SR method, whereby the specific sequence is amplified by the concerted action of reverse transcriptase and RNA polymerase. These methods involve a chain reaction, wherein a promoter sequence-containing primer for a specific sequence in the target RNA, reverse transcriptase, and Ribonuclease H are used to synthesize double-stranded DNA containing the promoter sequence, and this double-stranded DNA is used as a template for RNA polymerase-catalyzed synthesis of RNA containing the specific sequence, while the RNA in turn becomes a template for synthesis of double-stranded DNA containing the promoter sequence. The NASBA method and 3SR method can accomplish nucleic acid amplification at a constant temperature, and are therefore considered to be methods suitable for automation. In this situation, the presence of mecA gene as well as its existing amount can be measured, for example, by qualitative or quantitative determination of a mRNA coding for PBP-2'. Moreover, since this mRNA is a gene from which PBP-2' is expressed, it presents in an amount much larger than the number of copies of mecA gene located on the chromosomal DNA. Thus, the mecA gene can be detected without culturing the bacteria from a specimen, making this method useful for rapid diagnosis. At this time, in the amplification of the above specific sequence by the NASBA method or the like, an oligonucleotide having high specificity to the above specific sequence is required. Moreover, in order to perform detection and identification with high sensitivity, an oligonucleotide that has high specificity to the target RNA is required. Therefore, an attempt to detect the mecA gene located on the chromosomal DNA of *Staphylococcus aureus* by the NASBA method using specific oligonucleotide sequences has been made. However, since the NASBA method or the like involves amplification reaction at relatively low temperature (for example, 41° C.), the target RNA forms an intramolecular structure which inhibits binding of the primer, and may reduce the reaction efficiency. Consequently, a procedure of heat denaturation of the target RNA prior to the amplification reaction was required to break down the intramolecular structure of the target RNA, thereby to improve the primer binding efficiency. In addition, even in the case where detection of RNA is carried out at a low temperature, an oligonucleotide capable of binding to RNA which has formed the above-mentioned intramolecular structure is required.

Therefore, the first object of the present invention is to provide oligonucleotides that are useful in specific cleavage, amplification, or the like, as well as highly sensitive detection and identification of the mecA gene coding for cell wall composing-protein PBP-2' produced by MRSA or RNA derived from said gene. In addition, the present invention provides oligonucleotide sequences useful in a pharmaceutical composition for inhibiting RNA reverse transcription or translation.

The second object of the present invention is to provide a preferable combination of oligonucleotides useful in specific amplification of RNA derived from the mecA gene coding for cell wall composing-protein PBP-2' produced by methicillin-resistant *Staphylococcus aureus* at a relatively low temperature (e.g., 41° C.), as well as for the highly sensitive detection and identification thereof.

DETAILED DESCRIPTION OF THE INVENTION

The invention which has been accomplished to achieve the first object, relates to an oligonucleotide for cleavage, detection or amplification of the mecA gene, a gene element of methicillin-resistant *Staphylococcus aureus* (MRSA), or RNA derived from said gene, which oligonucleotide is capable of binding specifically to said mecA gene or RNA derived therefrom, and comprises at least 10 contiguous bases of any of the sequences listed as SEQ. ID. Nos. 1 to 17, or an oligonucleotide complementary to said oligonucleotide.

In one embodiment, the oligonucleotide is an oligonucleotide primer for DNA elongation reaction.

In another embodiment, the oligonucleotide is an oligonucleotide probe a portion of which is modified or labeled with a detectable marker.

In another embodiment, the oligonucleotide is a synthetic oligonucleotide in which a portion of its base(s) is(are) modified without impairing the function of said oligonucleotide as an oligonucleotide probe.

The oligonucleotides of the invention, which have been accomplished to achieve the first object, are oligonucleotides that complementarily bind in a specific manner to intramolecular structure-free regions of the target RNA in the aforementioned RNA amplification, and they are capable of binding specifically to the target RNA without the heat denaturation described above. In this manner, the present invention provides oligonucleotides that binds to intramolecular structure-free regions of the RNA derived from the mecA gene coding for PBP-2' at a relatively low and constant temperature (35–50° C., and preferably 41° C.), which are useful for specific cleavage, amplification, detection or the like of the mecA gene. More specifically, the present invention relates to oligonucleotides which accomplish rapidly and highly sensitive detection by their use as oligonucleotide primers for amplifying the above target DNA with PCR, oligonucleotide primers for amplifying the above target RNA with NASBA or the like, and an oligonucleotide probe for detecting the target nucleic acid without or after these amplifications. In this connection, recently, in order to improve genetic detection technology, developments of new chemically synthesized substances, which would not impair the function of an oligonucleotide probe to recognize a complementary sequence based on adenine, guanine, cytosine and thymine (or uracil) bases have been carried out. One example of such substances includes peptide nucleic acid (PNA) in which the sugar and phosphoric acid skeletons that provides the skeleton structure of nucleic acid DNA have been replaced with a polyamide skeleton. Thus, oligonucleotides that have been modified by a substance such as PNA to an extent that would not impair their base sequences recognizing-function are also included in the detecting probes of the present invention.

SEQ ID Nos.1 through 17 illustrate the oligonucleotides of the present invention useful in cleavage, amplification, detection or the like of RNA derived from the mecA gene. In this connection, RNA derived from the mecA gene also includes RNA that has been produced by using these genes as templates. Although each of the oligonucleotides of the present invention may include entire base sequence of any of SEQ ID Nos. 1 to 17, since an order of 10 bases is adequate for specific binding to mecA gene, these oligonucleotides can be oligonucleotides comprising at least 10 contiguous bases of the described sequences, and may also be their complementary oligonucleotides.

The oligonucleotides of the present invention can be used, for example, as an oligonucleotide primer for nucleic acid amplification. If a nucleic acid amplification method is carried out using the oligonucleotide of the present invention as the primer, only the target nucleic acid, namely mecA, can be amplified. Although examples of amplification methods include PCR, LCR, NASBA and 3SR, nucleic acid amplification methods that can be carried out at a constant temperature such as LCR, NASBA and 3SR are particularly preferable. MRSA can be detected by detecting the amplification product by various methods. In this case, any of the above oligonucleotides other than the oligonucleotide used in the amplification may be used as the probe, and the fragment of the amplified specific sequence can be confirmed by electrophoresis or the like.

The oligonucleotides of the present invention can be used as probes by, for example, modifying portions or labeling them with a detectable marker. When detecting the target nucleic acid, the oligonucleotide of the present invention labeled with the detectable marker may be hybridized to a single-stranded target nucleic acid, after which the hybridized probe can be detected via the marker. The marker detection may be carried out by a method suitable for the particular marker and, for example, when using an intercalator fluorescent dye for labeling the oligonucleotide, a dye with the property of exhibiting increased fluorescent intensity by intercalation in the double-stranded nucleic acid comprising the target nucleic acid and the oligonucleotide probe may be used in order to allow easy detection of only the hybridized probe without removal of the probe that has not hybridized to the target nucleic acid. When using a common fluorescent dye as the marker, the marker may be detected after removal of the probe that has not hybridized to the target nucleic acid. For the detection, the target nucleic acid in the sample is preferably amplified to a detectable amount by a nucleic acid amplification method such as PCR, NASBA or 3SR method, among which isothermal nucleic acid amplification methods such as the NASBA and 3SR methods are most preferable. When incorporating the nucleotide-labeled probe in the reaction solution during the amplification, it is especially preferable to modify the probe by, for example, adding glycolic acid to the 3'-end so that the probe will not function as a nucleotide primer.

An embodiment of the invention relates to a detection method employing a RNA amplification process, which comprises the steps of: forming a cDNA with a RNA-dependent DNA polymerase using a specific sequence of a RNA derived from mecA gene, a gene element of MRSA, present in a sample as a template, with a first primer having a sequence homologous to said specific sequence and a second primer having a sequence complementary to said specific sequence, wherein either the first or second primer has a sequence having the RNA polymerase promoter sequence added at its 5'-region, thereby producing a RNA-DNA double-strand; digesting the RNA of said RNA-DNA double-strand with Ribonuclease H to form a single-stranded DNA; and then forming a double-stranded DNA that includes a promoter sequence allowing transcription of said RNA sequence or a RNA comprising a sequence complementary to said RNA sequence with a DNA-dependent DNA polymerase using said single-stranded DNA as a template, said double-stranded DNA produces a RNA transcription product in the presence of a RNA polymerase, and said RNA transcription product is subsequently used as the template for the single-stranded DNA production with said RNA-dependent DNA polymerase; characterized in that the oligonucleotide of SEQ. ID. No.18 is used as the first primer and the oligonucleotide of any of SEQ. ID. Nos.19 to 21 is used as the second primer, or the oligonucleotide of SEQ. ID. No.22 is used as the first primer and the oligonucleotide of SEQ. ID. Nos.23 or 24 is used as the second primer, or the oligonucleotide of SEQ. ID. No.25 is used as the first primer and the oligonucleotide of SEQ. ID. Nos.23 or 24 is used as the second primer.

An embodiment of the invention relates to the detection method characterized in that said first primer is an oligonucleotide comprising at least 10 contiguous bases of the sequence of SEQ. ID. Nos.18, 22 or 25.

An embodiment of the invention relates to the detection method characterized in that said second primer is an oligonucleotide comprising at least 10 contiguous bases of the sequence of SEQ. ID. Nos.19, 20, 21, 23 or 24.

An embodiment of the invention relates to a detection method for a methicillin-resistant *Staphylococcus aureus* (MRSA), which comprises the steps of: conducting the RNA amplification process in the presence of an oligonucleotide probe labeled with an intercalator fluorescent dye, wherein the sequence of said probe is complementary to at least a portion of said RNA transcription product, and complementary binding of said probe to said RNA transcription product results in a change of the fluorescent property relative to that of a situation where a complex formation is absent; and then measuring the fluorescence intensity of the reaction solution.

The present invention provides a combination of oligonucleotides for amplifying and detecting RNA derived from the mecA gene of methicillin-resistant *Staphylococcus aureus* at a relatively low and constant temperature (35–50° C., and preferably 41° C.). Namely, the present invention provides a combination of an oligonucleotide primer for amplification of RNA derived from mecA gene and an oligonucleotide probe for detection and thereby provides a simple, rapidly and highly sensitive mecA gene detection method and a detection kit for clinical examination or the like using said combination.

In one mode for carrying out the present invention, a second primer (a sequence complementary to the 3' end region of a specific sequence of the target RNA) complementary binds to the specific sequence of RNA derived from mecA gene of methicillin-resistant *Staphylococcus aureus* present in a sample as a template, and cDNA is produced by an extension reaction with RNA-dependent DNA polymerase to form a RNA-DNA double-strand, after which the RNA of the RNA-DNA double-strand is digested with Ribonuclease H to produce a single-stranded DNA. Next, a first primer (a sequence homologous to the 5' end region of the target RNA, and including the RNA polymerase promoter sequence added at the 5' end) complementary binds to the single-stranded DNA, to produce a double-stranded DNA having a promoter sequence allowing transcription of RNA comprising a sequence homologous to the target RNA sequence, using DNA-dependent DNA polymerase. The double-stranded DNA is then used for amplification of the RNA transcription product comprising the sequence homologous to the target RNA sequence in the presence of RNA polymerase. The present invention is thus characterized by the use of an oligonucleotide of SEQ ID Nos. 18, 22 or 25 for the first primer and an oligonucleotide of SEQ ID Nos. 19, 20, 21, 23 or 24 for the second primer. Although the first and second primers may be the entire length of their respective sequences, combinations of oligonucleotides comprising at least 10 contiguous bases within each sequence may also be used.

In the above mode of the present invention, the target RNA must be cleaved at the 5' end of the specific sequence. The method of cleaving the target RNA is preferably a method in which an oligonucleotide (cleaving oligonucleotide) with a sequence complementary to a region overlapping and adjacent to the 5'-end of the specific sequence is added, thereby cleaving the target RNA with Ribonuclease H or the like. The 3'-end of the cleaving oligonucleotide is preferably treated by amination, for example, to prevent it from functioning as an oligonucleotide primer.

In the above mode of the present invention, the amplification process is preferably carried out in the presence of an oligonucleotide probe (detecting oligonucleotide probe) labeled with an intercalator fluorescent dye having a sequence complementary to at least a portion of the RNA transcription product. Complementary binding of the probe to the RNA transcription product results in a change in the fluorescent property compared to a situation where the complex formation is absent, so that the fluorescence intensity of the reaction solution may be measured. In addition, when a labeled oligonucleotide probe is incorporated during the amplification process, it is particularly preferable to modify the probe by, for example, addition of glycolic acid to the 3'-end, to prevent it from functioning as a primer in the extension reaction. Examples of oligonucleotides that can be used for the oligonucleotide probe for detection include the sequences described in SEQ ID Nos. 20 or 29.

In an another mode for carrying out the present invention, a second primer (a sequence complementary to the target RNA, and including the RNA polymerase promoter sequence added at the 5' region) complementary binds to the specific sequence of RNA derived from the mecA gene of methicillin-resistant *Staphylococcus aureus* present in a sample as a template, and cDNA is produced by extension reaction with RNA-dependent DNA polymerase to form a RNA-DNA double-strand, after which the RNA of the RNA-DNA double-strand is digested with Ribonuclease H to produce a single-stranded DNA. Next, a first primer (a sequence homologous to the 5' end region of the target RNA) complementary binds to the single-stranded DNA, to produce a double-stranded DNA having a promoter allowing the transcription of RNA comprising a sequence complementary to the target RNA sequence, using DNA-dependent DNA polymerase. The double-stranded DNA is then used for amplification of the RNA transcription product comprising the sequence complementary to the target RNA sequence in the presence of RNA polymerase. The present invention is thus characterized by the use of an oligonucleotide of SEQ ID Nos.18, 22 or 25 for the first primer and an oligonucleotide of SEQ ID Nos.19, 20, 21, 23 or 24 for the second primer. Although the first and second primers may be the entire length of their respective sequences, combinations of oligonucleotides comprising at least 10 contiguous bases within each sequence may also be used.

In the above mode of the present invention, the amplification process is preferably carried out in the presence of an oligonucleotide probe (detecting oligonucleotide probe) labeled with an intercalator fluorescent dye having a sequence complementary to at least a portion of the RNA transcription product. Complementary binding of the probe to the RNA transcription product results in a change in the fluorescent property compared to a situation where the complex formation is absent, so that the fluorescence intensity of the reaction solution may be measured. In addition, when a labeled oligonucleotide probe is incorporated during the amplification process, it is particularly preferable to modify the probe by, for example, addition of glycolic acid to the 3'-end, to prevent it from functioning as a primer in the extension reaction. Examples of oligonucleotides that can be used for the oligonucleotide probe for detection include the sequences complementary to the sequences described in SEQ ID Nos.20 or 29.

EXAMPLES

Figure 1:
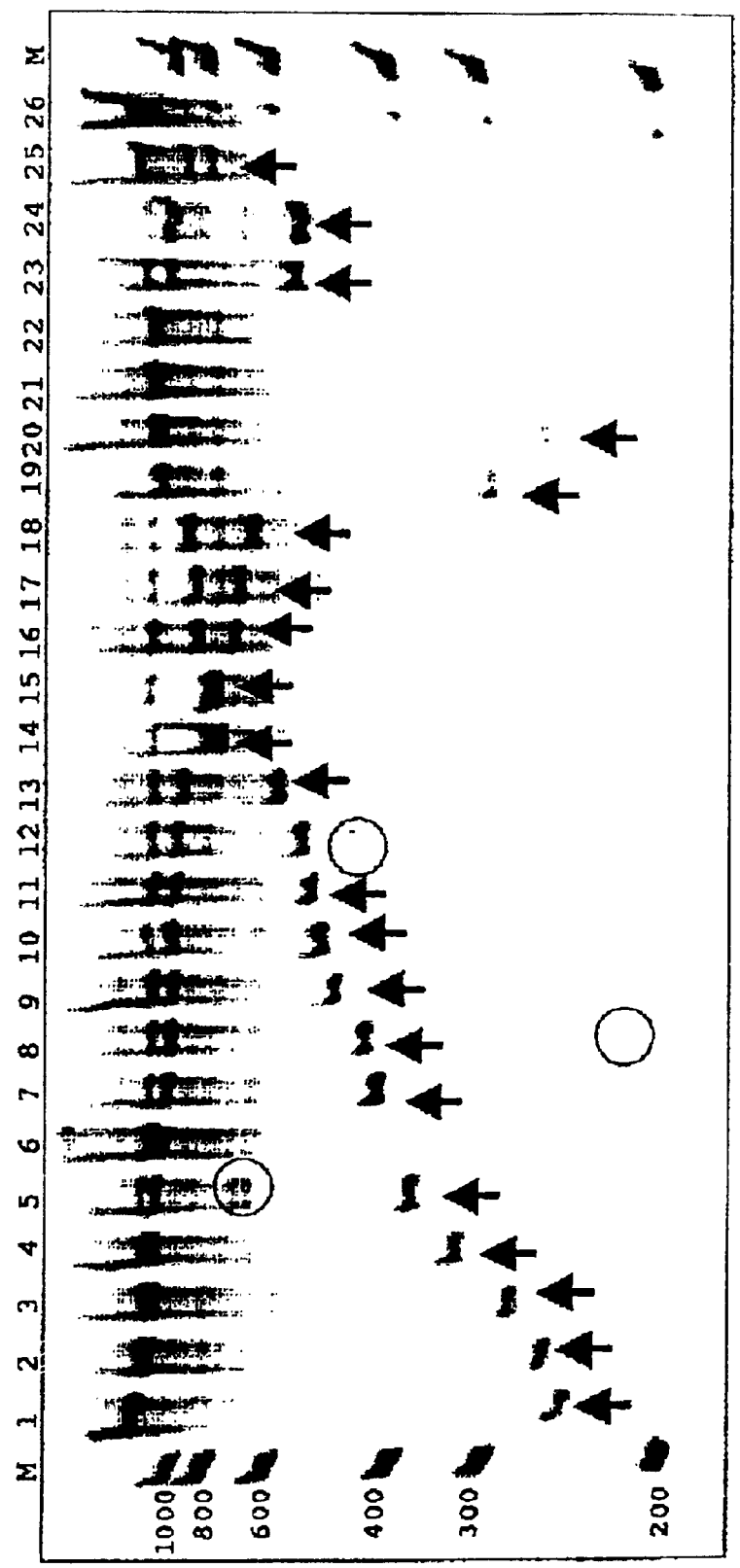
FIG. 1 is a photograph (black and white inverted) showing the status of an oligonucleotide, which illustrates an electrophoresis image of 7 M urea-5% polyacrylamide gel electrophoresis for a sample after performing a binding test to mecA-RNA at 41° C., using oligonucleotides designed for an intramolecular structure-free region of mecA-RNA coding for PBP-2'. In this figure, lane M is the RNA marker, and lanes 1 through 25 are the numbers of the oligonucleotide solutions indicated in Example 1. Lane 26 represents the case without using an oligonucleotide.

The present invention will now be explained in greater detail by way of examples, with the understanding that the invention is not limited by these examples.

EXAMPLES 1

Specific binding of the oligonucleotides of the invention to mecA-RNA at 41° C. was examined. The mecA-RNA is a synthesized and purified RNA obtained by in vitro transcription using double-stranded DNA containing the mecA-RNA base sequence as the template.

First, a sample of a standard RNA (2016 mer) comprising base Nos. 1 to 2013 of mecA-RNA derived from PBP-2'(the RNA base sequence numbering is in accordance with Matsubashi, et al. FEBS Lett., 221, 167–171 (1987)) was quantified by ultraviolet absorption at 260 nm, and then diluted with an RNA diluent (10 mM Tris-HCl (pH 8.0), 0.1 mM EDTA, 0.5 U/μl RNase Inhibitor) to $2.0 \times 10^{-12}$ mol/μl.

Next, the following compositions were dispensed into 0.5 ml volume PCR tubes (GeneAmp Thin-Walled Reaction™ Tubes; Perkin-Elmer Co., Ltd.).

0.90 μl of 1 M Tris-HCl buffer (pH 8.6)
0.20 μl of 1 M magnesium chloride
0.67 μl of 2 M potassium chloride
0.15 μl of 0.1 M DTT
0.33 μl of 119 U/μl RNase inhibitor
9.95 μl of distilled water
0.6 μl of 2 pmol/μl mecA-RNA sample
1.2 μl of 1.0 μM oligonucleotide solution In this context, one of the oligonucleotide solutions numbered below was used as the oligonucleotide solution.

1. Oligonucleotide complementary to base Nos.241 to 261 of mecA-RNA (SEQ ID No. 1)
2. Oligonucleotide complementary to base Nos.264 to 283 of mecA-RNA (SEQ ID No. 2)
3. oligonucleotide complementary to base Nos.296 to 315 of mecA-RNA (SEQ ID No. 3)
4. Oligonucleotide complementary to base Nos.349 to 368 of mecA-RNA (SEQ ID No. 4)
5. Oligonucleotide complementary to base Nos.402 to 421 of mecA-RNA
6. Oligonucleotide complementary to base Nos.425 to 444 of mecA-RNA
7. Oligonucleotide complementary to base Nos.456 to 475 of mecA-RNA (SEQ ID No. 5)
8. Oligonucleotide complementary to base Nos.499 to 480 of mecA-RNA
9. Oligonucleotide complementary to base Nos.551 to 532 of mecA-RNA (SEQ ID No. 6)
10. Oligonucleotide complementary to base Nos.556 to 575 of mecA-RNA (SEQ ID No. 7)
11. Oligonucleotide complementary to base Nos.581 to 600 of mecA-RNA (oligonucleotide of the 16th to 35th bases from the 5' end of the sequence shown in SEQ ID No. 8)
12. Oligonucleotide complementary to base Nos.606 to 625 of mecA-RNA
13. Oligonucleotide complementary to base Nos.672 to 691 of mecA-RNA (SEQ ID No. 9)
14. Oligonucleotide complementary to base Nos.941 to 961 of mecA-RNA (SEQ ID No. 10)
15. oligonucleotide complementary to base Nos.967 to 986 of mecA-RNA (SEQ ID No. 11)
16. Oligonucleotide complementary to base Nos.1134 to 1153 of mecA-RNA (SEQ ID No. 12)
17. Oligonucleotide complementary to base Nos.1154 to 1173 of mecA-RNA (SEQ ID No. 13)
18. Oligonucleotide complementary to base Nos.1221 to 1240 of mecA-RNA (SEQ ID No. 14)
19. Oligonucleotide complementary to base Nos.1656 to 1675 of mecA-RNA (SEQ ID No. 15)

20. Oligonucleotide complementary to base Nos.1701 to 1720 of mecA-RNA (SEQ ID No. 16)
21. Oligonucleotide complementary to base Nos.1852 to 1871 of mecA-RNA
22. Oligonucleotide complementary to base Nos.1906 to 1925 of mecA-RNA
23. Oligonucleotide complementary to base Nos.596 to 615 of mecA-RNA (oligonucleotide of the 1st to 20 the bases from the 5' end of the sequence shown in SEQ ID No. 8)
24. Oligonucleotide complementary to base Nos.577 to 615 of mecA-RNA (SEQ ID No. 8)
25. Oligonucleotide complementary to base Nos.1087 to 1100 of mecA-RNA (SEQ ID No. 17)

The reaction solutions were then incubated at 41° C. for 5 minutes, 1 µl of AMV-Rtase(Takara Shuzo Co., Ltd.; AMV-RTase is an enzyme that cleaves the RNA of DNA/RNA double strands) was added, and the PCR tube was incubated at 41° C. for 15 minutes.

Polyacrylamide gel (acrylamide concentration: 5%, urea: 7 M) electrophoresis was conducted to confirm the cleaved fragments after the reaction. Dyeing after electrophoresis was carried out with a commercially available dye (SYBR Green IT™ (Takara Shuzo Co., Ltd.)). Upon binding of the oligonucleotide to the specific site of the target RNA, the RNA of the DNA/RNA double strands is cleaved by the ribonuclease H activity of AMV-Rtase, which allows observation of specific bands.

The results of electrophoresis are shown in FIG. 1. Regarding the bands newly appearing in each lane, in the lanes where two bands could be observed as a result of a specific cleavage with one of the employed oligonucleotide, bands with shorter length are indicated with arrows. In addition, the bands exhibiting significant non-specific cleavage are encircled. Among the above oligonucleotides, only oligonucleotide solutions containing SEQ ID Nos. 1 through 17 and SEQ ID No. 8 showed characteristic cleaved bands without significant non-specific cleavage, demonstrating that each of these oligonucleotides strongly binds to mecA-RNA at 41° C.

Results

As explained above, the oligonucleotides of the present invention are oligonucleotides that complementary bind to RNA derived from mecA-gene coding for PBP-2', even under conditions of relatively low and constant temperature (35–50° C., preferably 41° C.), which tend to produce an intramolecular structure in RNA and prevent binding of primers and probes thereto. Specific binding of the oligonucleotides is therefore possible without heat denaturation of the target RNA. The oligonucleotides of the invention are thus useful as oligonucleotides for cleavage, amplification, detection or the like of mecA-RNA, a gene element of MRSA, i.e. as oligonucleotide primers or oligonucleotide probes to be used in RNA amplification methods.

Furthermore, the oligonucleotides of the invention are also clearly useful for amplification and detection of the mecA gene. Oligonucleotides complementary to the above-mentioned oligonucleotides are also useful for amplification of double-stranded DNA by the PCR method, or for detection of cDNA obtained by reverse transcription of RNA.

The oligonucleotides of the invention are not limited to the specifically listed base sequences(20 mers), and they may be oligonucleotides comprising at least 10 or more contiguous bases within those sequences. This is obvious from the fact that 10 mer base sequences are sufficient to ensure adequate specificity of primers or probes to target nucleic acids under relatively low temperature condition (preferably, at 41° C.).

EXAMPLE 2

Specific amplification of target RNA was carried out using a combination of oligonucleotide primers according to the present invention. The mecA-RNA is a synthesized and purified RNA obtained by in vitro transcription using double-stranded DNA containing the mecA-RNA base sequence as the template.

(1) A sample of a standard RNA (2016 mer) comprising base Nos. 1 to 2013 of mecA-RNA derived from PBP-2' (the RNA base sequence numbering is in accordance with Matsubashi, et al. FEBS Lett., 221, 167–171 (1987)) was quantified by ultraviolet absorption at 260 nm, and then diluted with an RNA diluent (10 mM Tris-HCl (pH 8.0), 0.1 mM EDTA, 0.5 U/µl RNase Inhibitor, 5.0 mM DTT) to $1.0 \times 10^4$ copies/2.5µl.

In the control testing group, only the diluent was used (Nega).

(2) 23.3 µl of a reaction liquid having the composition indicated below was dispensed into 0.5 ml volume PCR tubes (Gene Amp Thin-Walled Reaction Tubes, Perkin-Elmer) followed by addition of 2.5 µl of the above RNA sample.

Composition of Reaction Liquid (concentrations refer to the final concentrations in the reaction system following addition of enzyme solution)

60.0 mM Tris-HCl buffer (pH 8.6)
13.0 mM magnesium chloride
90.0 mM potassium chloride
1.0 mM DTT
0.25 mM each of dATP, dCTP, dGTP and dTTP
3.0 mM each of ATP, GTP and UTP
2.25 mM GTP
3.6 mM ITP
1.0 µM each of the first and second primers
0.16 µM of a cleaving oligonucleotide probe (oligonucleotide for cleaving the target RNA at a position to which the first primer is capable to bind; the 3' end thereof is aminated)
39 U ribonuclease inhibitor (Takara Shuzo)
15.0% DMSO
Distilled water for adjusting volume One of the combinations numbered below was used for the combination of the first primer, the second primer and the cleaving probe.

1. As for the first primer, oligonucleotide of the 4th to 15th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.19; and as for the cleaving probe, the oligonucleotide shown in SEQ ID No.26.
2. As for the first primer, oligonucleotide of the 4th to 15th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.20; and as for the cleaving probe, the oligonucleotide shown in SEQ ID No.26.
3. As for the first primer, oligonucleotide of the 4th to 15th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.21; and as for the cleaving probe, the oligonucleotide shown in SEQ ID No.26.
4. As for the first primer, oligonucleotide of the 4th to 28th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.20; and as for the cleaving probe, the oligonucleotide shown in SEQ ID No.26.
5. As for the first primer, oligonucleotide of the 4th to 28th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.21; and as for the cleaving probe, the oligonucleotide shown in SEQ ID No.26.
6. As for the first primer, oligonucleotide of the 1st to 25th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.20; and as for the cleaving probe, the oligonucleotide shown in SEQ ID No.26.
7. As for the first primer, oligonucleotide of the 1st to 25th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.21; and as for the cleaving probe, the oligonucleotide shown in SEQ ID No.26.
8. As for the first primer, oligonucleotide of the 4th to 28th bases from the 5' end of the sequence shown in SEQ ID No.22, wherein the promoter sequence of T7 polymerase shown in SEQ ID No.30 is added to its 5' end; as for the second primer, the oligonucleotide shown in SEQ ID No.23; and as for the cleaving probe, the oligonucleotide shown in SEQ ID No.27.
9. As for the first primer, oligonucleotide of the 4th to 28th bases from the 5' end of the sequence shown in SEQ ID No.22, wherein the promoter sequence of T7 polymerase shown in SEQ ID No.30 is added to its 5' end; as for the second primer, the oligonucleotide shown in SEQ ID No.24; and as for the cleaving probe, the oligonucleotide shown in SEQ ID No.27.
10. As for the first primer, oligonucleotide of the 1st to 25th bases from the 5' end of the sequence shown in SEQ ID No.22, wherein the promoter sequence of T7 polymerase shown in SEQ ID No.30 is added to its 5' end; as for the second primer, the oligonucleotide shown in SEQ ID No.23; and as for the cleaving probe, the oligonucleotide shown in SEQ ID No.27.
11. As for the first primer, oligonucleotide of the 1st to 25th bases from the 5' end of the sequence shown in SEQ ID No.22, wherein the promoter sequence of T7 polymerase shown in SEQ ID No.30 is added to its 5' end; as for the second primer, the oligonucleotide shown in SEQ ID No.24; and as for the cleaving probe, the oligonucleotide shown in SEQ ID No.27.
12. As for the first primer, oligonucleotide of the 4th to 28th bases from the 5' end of the sequence shown in SEQ ID No.25, wherein the promoter sequence of T7 polymerase shown in SEQ ID No.30 is added to its 5' end; as for the second primer, the oligonucleotide shown in SEQ ID No.23; and as for the cleaving probe, the oligonucleotide shown in SEQ ID No.28.
13. As for the first primer, oligonucleotide of the 4th to 28th bases from the 5' end of the sequence shown in SEQ ID No.25, wherein the promoter sequence of T7 polymerase shown in SEQ ID No.30 is added to its 5' end; as for the second primer, the oligonucleotide shown in SEQ ID No.24; and as for the cleaving probe, the oligonucleotide shown in SEQ ID No.28.
14. As for the first primer, oligonucleotide of the 1st to 25th bases from the 5' end of the sequence shown in SEQ ID No.25, wherein the promoter sequence of T7 polymerase shown in SEQ ID No.30 is added to its 5' end; as for the second primer, the oligonucleotide shown in SEQ ID No.23; and as for the cleaving probe, the oligonucleotide shown in SEQ ID No.28.
15. As for the first primer, oligonucleotide of the 1st to 25th bases from the 5' end of the sequence shown in SEQ ID No.25, wherein the promoter sequence of T7 polymerase shown in SEQ ID No.30 is added to its 5' end; as for the second primer, the oligonucleotide shown in SEQ ID No.24; and as for the cleaving probe, the oligonucleotide shown in SEQ ID No.28.

(3) After incubating the above reaction solutions for 5 minutes at 41° C., 4.2 µl of enzyme liquid having the following composition and pre-incubated for 2 minutes at 41° C. was added.

Composition of Enzyme Liquid (final concentrations during reaction)
1.7% sorbitol
8 units of AMV reverse transcriptase (Takara Shuzo)
142 units of T7 RNA polymerase (Gibco)
3 µg of bovine serum albumin
Distilled water for adjusting volume (4) After which, the PCR tubes were incubated for 90 minutes at 41° C., and then the specific amplification products were analyzed by electrophoresis using 4% agarose gel.

(5) A commercially available dye (SYBR Green II™: Takara Shuzo) was used for staining after electrophoresis.

Figure 2:
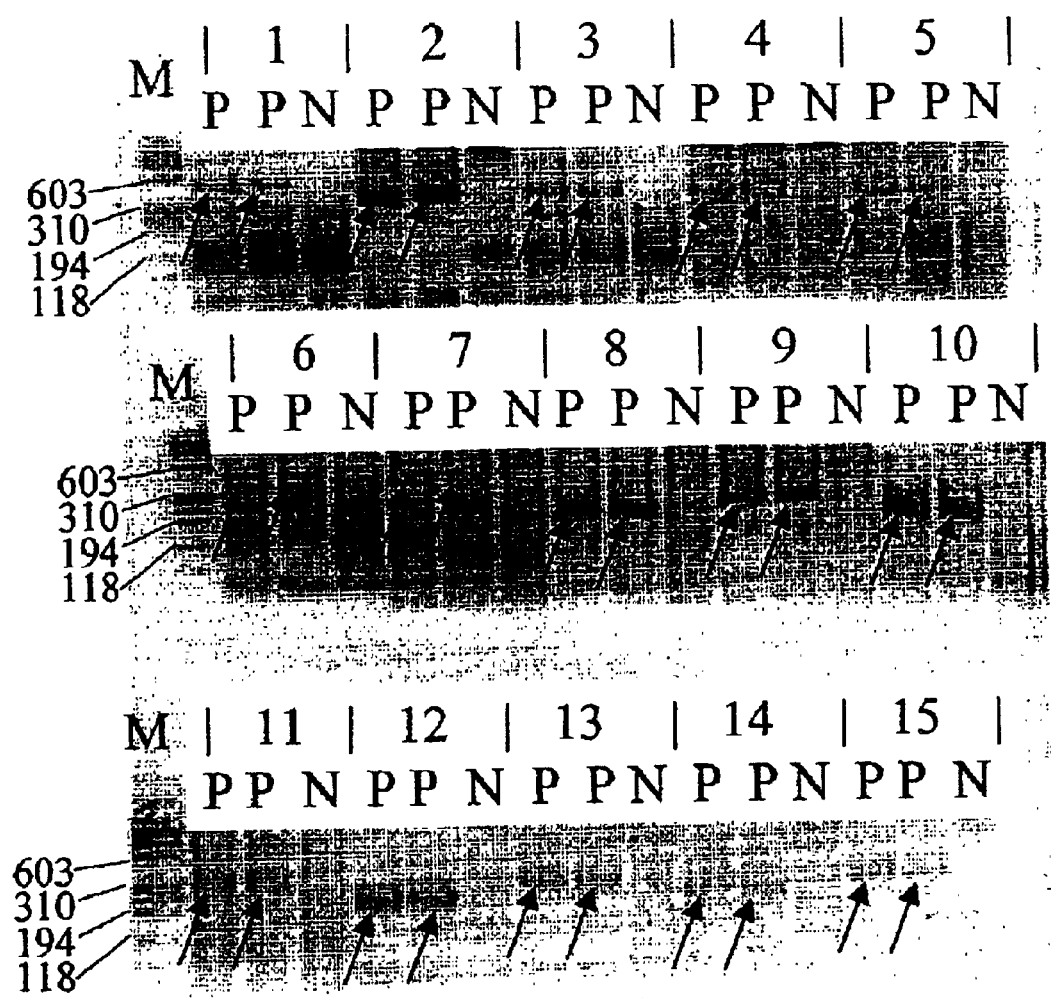
FIG. 2 illustrates the results of performing an RNA amplification reaction with various combinations of primers in Example 2. In the figure, P represents the case where a RNA sample of an initial RNA amount of $10^5$ copies/30 μl is used, and N represents the case where only diluent is used instead of RNA sample. In addition, lane M indicates the molecular weight marker, while 1 to 15 indicate the numbers of the combinations of primer and probe in Example 2.

The results of electrophoresis are shown in FIG. 2 (black and white inverted photograph). For all of the combinations, specific RNA amplification products (indicated with arrows) were obtained in the systems to which mecA-RNA was added. On the basis of this finding, these combinations of oligonucleotide primers were demonstrated as being useful in the amplification and detection of RNA derived from the mecA gene of methicillin-resistant *Staphylococcus aureus*.

EXAMPLE 3

Using the combination of oligonucleotide primers according to the present invention, the possibility of specific detection of mecA-RNA, the target RNA, was confirmed.

(1) A sample of a standard RNA (2016 mer) comprising base Nos. 1 to 2013 of mecA-RNA derived from PBP-2' (the RNA base sequence numbering is in accordance with Matsubashi, et al. FEBS Lett., 221, 167–171 (1987)) was quantified by ultraviolet absorption at 260 nm, and then diluted with an RNA diluent (10 mM Tris-HCl (pH 8.0), 0.1 mM EDTA, 0.5 U/µl RNase Inhibitor, 0.5 mM DTT) to $1.0 \times 10^6$ copies/2.5 µl or $1.0 \times 10^4$ copies/2.5µl In the control testing group, only the diluent was used (Nega).

(2) 23.3 µl of a reaction liquid having the composition indicated below was dispended into 0.5 ml volume PCR tubes (Gene Amp Thin-Walled Reaction Tubes, Perkin-Elmer) followed by addition of 2.5 µl of the above RNA sample (mecA-RNA).

Figure 3:
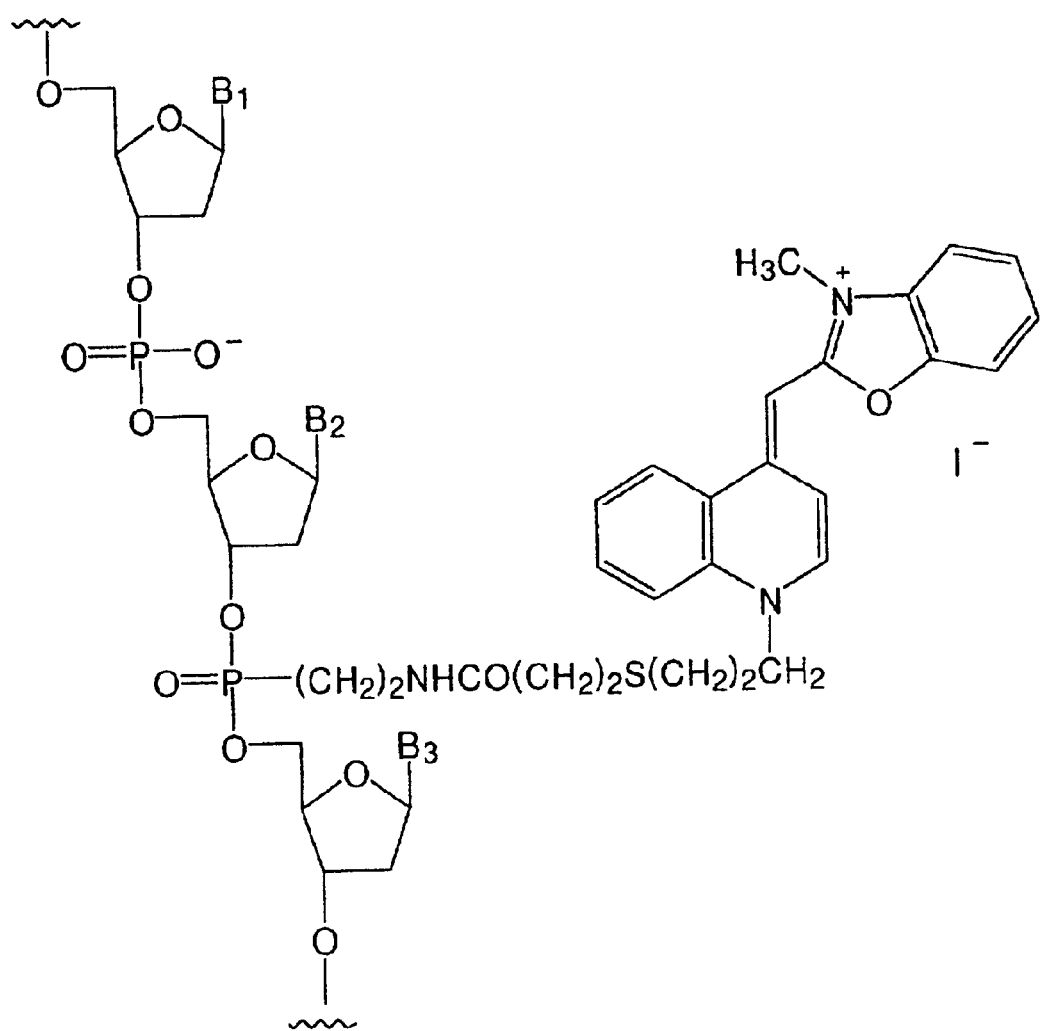
FIG. 3 illustrates the chemical structures of the intercalator fluorescent dye portions of the oligonucleotides labeled with the intercalator fluorescent dye used in Example 3. $B_1$–$B_3$ represent nucleic acid bases.
Figure 4:
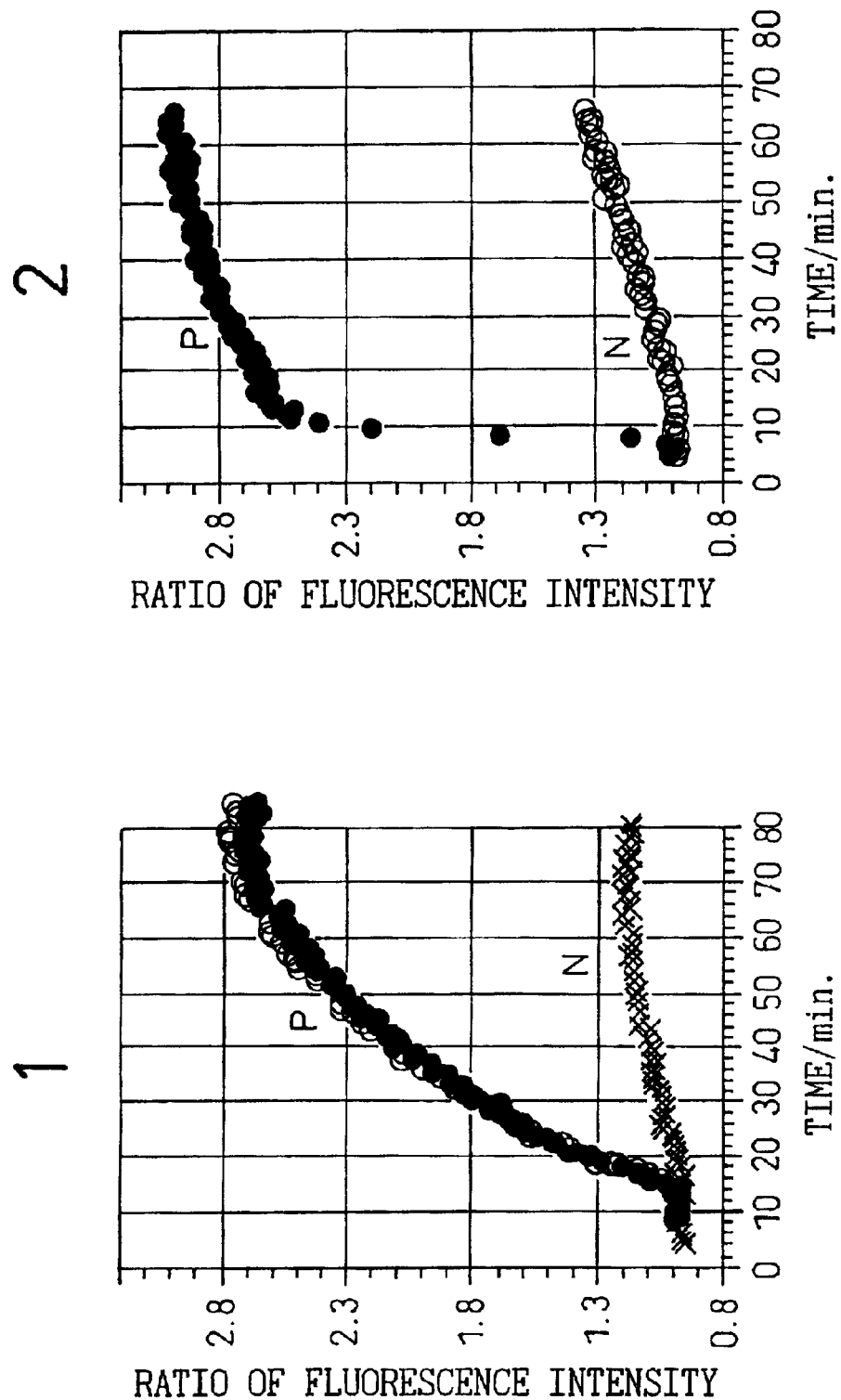
FIG. 4 illustrates the relationship between the reaction time and the fluorescence increasing rate. 1 and 2 represent the numbers of combinations of primers and probes in Example 3. In the graphs, for combination 1, P represents the case where a RNA sample of an initial RNA amount of $10^6$ copies/30 μl is used and, for combination 2, P represents the case where a RNA sample of an initial RNA amount of $10^4$ copies/30 μl is used. N represents the case where only diluent is used instead of RNA sample.

Composition of Reaction Liquid (concentrations refer to the final concentrations in the reaction system following addition of enzyme solution)
60.0 mM Tris-HCl buffer (pH 8.6)
13.0 mM magnesium chloride
90.0 mM potassium chloride
1.0 mM DTT
0.25 mM each of dATP, dCTP, dGTP and dTTP
3.0 mM each of ATP, GTP and UTP 2.25 mM GTP
3.6 mM ITP
1.0 μM of the first oligonucleotide primer
1.0 μM of the second oligonucleotide primer
0.16 μM cleaving oligonucleotide probe (oligonucleotide for cleaving the target RNA at a position to which the first primer is capable to bind; its 3' end is aminated)
25.0 nM of oligonucleotide probe for detection labeled with intercalator fluorescent dye(FIG. 3) (MRSH-YO; its 3' end modified with glycolic acid)
39 U ribonuclease inhibitor (Takara Shuzo)
15.0% DMSO
Distilled water for adjusting volume
One of the combinations numbered below was used for the combination of primers and probe.
1. As for the first primer, oligonucleotide of the 4th to 15th bases from the 5' end of the sequence shown in SEQ ID No.18, wherein the promoter sequence of T7 polymerase shown in SEQ ID No.30 is added to its 5' end; as for the second primer, the oligonucleotide shown in SEQ ID No.19; as for the cleaving probe, the oligonucleotide shown in SEQ ID No.26, and as for the probe for detection, the oligonucleotide shown in SEQ ID No.20.
2. As for the first primer, oligonucleotide of the 1st to 25th bases from the 5' end of the sequence shown in SEQ ID No.25, wherein the promoter sequence of T7 polymerase shown in SEQ ID No.30 is added to its 5' end; as for the second primer, the oligonucleotide shown in SEQ ID No.24; as for the cleaving probe, the oligonucleotide shown in SEQ ID No.28; and as for the detecting probe, the oligonucleotide shown in SEQ ID No.29.
(3) After incubating the above reaction solution for 4 minutes at 41° C., 4.2 μl of enzyme liquid having the following composition and pre-incubated for 2 minutes at 41° C. were added.
Composition of Enzyme Liquid (final concentrations during reaction)
1.7% sorbitol
8 units of AMV reverse transcriptase (Takara Shuzo)
142 units of T7 RNA polymerase (Gibco)
3 μg of bovine serum albumin
Distilled water for adjusting volume
(4) Next, using a temperature-controllable fluorescent spectrophotometer capable of directly measuring PCR tubes, periodic measurement of the fluorescence intensity of the reaction solution incubated at 41° C. with an excitation wavelength of 470 nm and a fluorescent wavelength of 510 nm was carried out. FIG. 4 shows the periodic changes in the fluorescence intensity ratio (fluorescence intensity at predetermined time/background fluorescence intensity) of the sample, where enzyme was added at 0 minutes The RNA sample concentrations were, for combination 1, $10^6$ copies/30 μl, and for combination 2, $10^4$ copies/30 μl.
In the system in which mecA-RNA was added to targeted RNA, specific fluorescent sensitization was obtained. On the basis of this finding, the combination of oligonucleotides of the present invention were demonstrated as being capable to specifically amplify and detect RNA derived from mecA gene.

EXAMPLE 4

Figure 5:
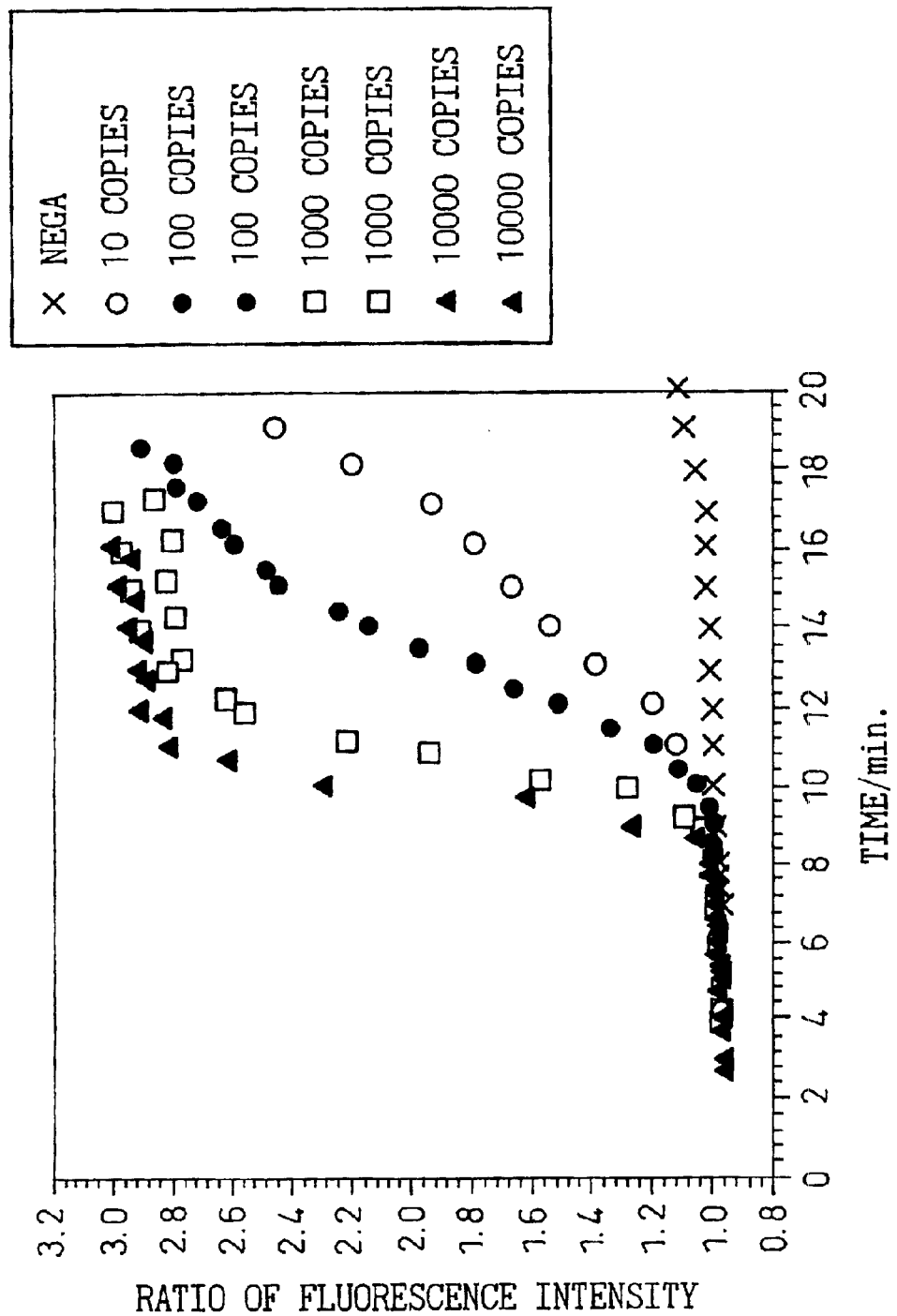
FIG. 5 illustrates a graph showing an increase in the fluorescence increasing rate with respect to the reaction time and the formation of RNA at initial RNA amounts ranging from $10^4$ copies/30 μl to 10 copies/30 μl as measured in Example 4. Nega indicates the use of only diluent instead of a RNA sample.

A combination of oligonucleotide primers according to the invention was used for specific detection of different initial copy numbers of the target RNA.
(1) A sample of a standard RNA (2016 mer) comprising base Nos. 1 to 2013 of mecA-RNA derived from PBP-2' (the RNA base sequence numbering is in accordance with Matsubashi, et al. FEBS Lett., 221, 167–171 (1987)) was quantified by ultraviolet absorption at 260 nm, and then diluted with an RNA diluent (10 mM Tris-HCl (pH 8.0), 0.1 mM EDTA, 0.5 U/μl RNase Inhibitor, 5.0 mM DTT) to concentrations ranging from $1.0 \times 10^4$ copies/2.5μl to 10 copies/2.5μl. In the control testing group, only the diluent was used (Nega).
(2) 23.3 μl of a reaction liquid having the composition indicated below was dispended into 0.5 ml volume PCR tubes (Gene Amp Thin-Walled Reaction Tubes, Perkin-Elmer) followed by addition of 2.5 l of the above RNA sample (mecA-RNA).
Composition of Reaction Liquid (concentrations refer to the final concentrations in the reaction system following addition of enzyme solution)
60.0 mM Tris-HCl buffer (pH 8.6)
13.0 mM magnesium chloride
90.0 mM potassium chloride
1.0 mM DTT
0.25 mM each of dATP, dCTP, dGTP and dTTP
3.0 mM each of ATP, CTP and UTP
2.25 mM GTP
3.6 mM ITP
1.0 μM of the first primer(oligonucleotide of the 4th to 28th bases from the 5' end of the sequence shown in SEQ ID No.25, wherein the promoter sequence of T7 polymerase shown in SEQ ID No.30 is added to its 5' end 1.0 μM of the second oligonucleotide primer (oligonucleotide of the 1st to 18th bases of from 5' end of the sequence shown in SEQ ID No.23)
0.16 μM cleaving oligonucleotide probe (SEQ ID No. 28: oligonucleotide for cleaving the target RNA at a position to which the first primer is able to bind, wherein its 3' end is aminated)
25.0 nM of oligonucleotide probe for detection labeled with intercalator fluorescent pigment (FIG. 3) (MRSH-YO; its oligonucleotide sequence is shown in SEQ ID No.29, and its 3' end is modified with glycolic acid)
39 U ribonuclease inhibitor (Takara Shuzo)
15.0% DMSO
Distilled water for adjusting volume
(3) After incubating the above reaction solution for 4 minutes at 41° C., 4.2 μl of enzyme liquid having the following composition and pre-incubated for 2 minutes at 41° C. were added.
Composition of Enzyme Liquid (final concentrations during reaction)
1.7% sorbitol
8 units of AMV reverse transcriptase (Takara Shuzo)
142 units of T7 RNA polymerase (Gibco)
3 μg of bovine serum albumin
Distilled water for adjusting volume
(4) Next, using a temperature-controllable fluorescent spectrophotometer capable of directly measuring PCR tubes, periodic measurement of the fluorescence intensity of the reaction solution incubated at 41° C. with an excitation wavelength of 470 nm and a fluorescent wavelength of 510 nm was carried out. FIG. 5 shows the periodic changes in the fluorescence intensity ratio (fluorescence intensity at predetermined time/background fluorescence intensity) of the sample, where enzyme was added at 0 minutes. The RNA sample concentrations were 10 copies/30 μl to $10^4$ copies/30 μl.
A fluorescence profile depending on the initial concentration of the target RNA was obtained from FIG. 5, indicating that it is possible to measure the amount of RNA derived from the mecA gene present in unknown samples.

Results

As has been explained above, the present invention is useful as combinations of oligonucleotide primers and oligonucleotide probes which specifically bind to RNA derived from the mecA gene coding for PBP-2', and rapidly amplify and detect the target RNA even under relatively low and constant temperature (35–50° C. and preferably 41° C.) conditions in which RNA in a sample would form an intramolecular structure which inhibits the primer and probe binding.

In addition to the above, the combinations of oligonucleotides of the present invention are not only useful for mecA-RNA, but also as complementary sequences of the above oligonucleotides for detecting cDNA obtained by reverse transcription of RNA.

The base lengths of the oligonucleotides in the combinations of the present invention are not limited to the concretely described lengths, but rather include oligonucleotides comprised of at least 10 contiguous bases within these sequences. This is clear from the fact that a base sequence of about 10 mer is adequate for ensuring specificity of primer or probe to a target nucleic acid under relatively low temperature (preferably 41° C.) conditions.

What is claimed is:

1. A method for detecting methicillin-resisant *Staphylococcus aureus* (MRSA) in a sample, said method comprising the steps of:

(a) preparing a reaction mcomprising:

a sample;

a first oligonucleotide primer comprising (i) a portion of the mecA gene of MRSA, wherein said portion is a target sequence and (ii) an RNA polymerase promoter sequence attached to the 5'-end of the sequence in (i);

a second oligonucleotide primer;

an enzyme or a mixture of enzymes having (i) RNA-dependent DNA polymerase activity, (ii) ribonuclease activity that hydrolyzes RNA of an RNA-DNA hybrid without hydrolyzing single-stranded and double-stranded RNA or DNA, (iii) DNA-dependent DNA polymerase activity, and (iv) DNA-dependent RNA polymerase activity; and a cleaving oligonucleotide probe comprising a sequence complementary to a region overlapping with and adjacent to said target sequence;

(b) incubating said reaction mixture under conditions that allow the formation of a double-stranded cDNA product from the target sequence and the transcription of an RNA product from the double-stranded cDNA product; and (c) detecting the RNA product transcribed from the double-stranded cDNA product,, wherein:

(1) an oligonucleotide comprising at least 10 contiguous bases of the sequence recited in SEQ ID No:18 is used as the first primer, an oligonucleotide comprising least 10 contiguous bases of the sequence recited in any of SEQ ID No:19, 20 or 21 is used as the second primer, and an oligonucleotide comprising the sequence recited in SEQ ID No:26 is used as the cleaving probe, or (2) an oligonucleotide comprising at least 10 contiguous bases of the sequence recited in SEQ ID No:22 is used as the first primer, an oligonucleotide comprising at least 10 contiguous bases of the sequence recited in any of SEQ ID No:23 or 24 is used as the second primer, and an oligonucleotide comprising the sequence recited in SEQ ID No:27 is used as the cleaving probe, or (3) an oligonucleotide comprising at least 10 contiguous bases of the sequence recited in SEQ ID No:25 is used as the first primer, an oligonucleotide comprising at least 10 contiguous bases of the sequence recited in any of SEQ ID No:23 or 24 is used as the second primer, and an oligonucleotide comprising the sequence recited in SEQ ID No:28 is used as the cleaving probe.

2. The method of claim 1, wherein said RNA polymerase promoter sequence comprises the nucleotide sequence recited in SEQ ID No:30.

3. The method of claim 1, wherein the reaction mixture further comprises a detection probe comprising a sequence complementary to a portion of the RNA product transcribed from the double-stranded cDNA product, and wherein said detection probe is labeled with an intercalator fluorescent dye.

4. The method of claim 3, wherein said detection probe comprises a sequence of SEQ ID NO: 20 or SEQ ID NO: 29.

* * * * *